United States Patent [19]
Brandell

[11] Patent Number: 6,068,651
[45] Date of Patent: May 30, 2000

[54] ATRIAL DEFIBRILLATION LOCK OUT FEATURE

[75] Inventor: Brian Brandell, Minneapolis, Minn.

[73] Assignee: Pacesetter, Inc., Sunnyvale, Calif.

[21] Appl. No.: 09/048,914

[22] Filed: Mar. 26, 1998

[51] Int. Cl.[7] .................................................. A61N 1/39
[52] U.S. Cl. .............................................................. 607/5
[58] Field of Search .................................. 607/5, 6, 7, 8

[56] References Cited

U.S. PATENT DOCUMENTS

| | | | |
|---|---|---|---|
| 3,952,750 | 4/1976 | Mirowski . | |
| 4,884,575 | 12/1989 | Samders . | |
| 5,207,219 | 5/1993 | Adams et al. . | |
| 5,282,837 | 2/1994 | Adams et al. | 607/5 |
| 5,312,446 | 5/1994 | Holschbach et al. | 607/9 |
| 5,332,400 | 7/1994 | Alferness | 607/5 |
| 5,342,408 | 8/1994 | deCoriolis et al. | 607/32 |
| 5,350,404 | 9/1994 | Adams et al. | 607/5 |
| 5,464,431 | 11/1995 | Adams et al. | 607/4 |
| 5,490,862 | 2/1996 | Adams et al. | 607/6 |
| 5,527,344 | 6/1996 | Arzbaecher et al. | 607/3 |
| 5,554,175 | 9/1996 | Alferness | 607/5 |
| 5,630,838 | 5/1997 | Prutchi et al. | 607/116 |

*Primary Examiner*—Scott M. Getzow
*Attorney, Agent, or Firm*—Steven M. Mitchell

[57] ABSTRACT

An implantable atrial defibrillator for converting atrial arrhythmias into normal sinus rhythm includes a patient activated mode, a programmable safety timer, and means for deactivating the patient activated mode. The programmable safety timer starts counting down when AF is detected. If the safety timer times out before the patient activates delivery of an atrial defibrillation shock, the device will deactivate the atrial defibrillation function, and will not allow an atrial defibrillation shock to be delivered until the physician reactivates it with a programmer. This allows the physician to administer anticoagulants to the patient prior to atrial cardioversion. The preferred length of time between AF detection and lock out of the atrial defibrillation function is 24 hours.

19 Claims, 3 Drawing Sheets

ATRIAL DEFIBRILLATION LOCK OUT FEATURE

FIELD OF THE INVENTION

The present invention generally relates to an implantable device for applying cardioverting electrical energy to at least one atrium of a patient's heart in need of cardioversion and a patient controlled delivery of the cardioverting energy. The present invention is more particularly directed to a implantable atrial defibrillator which exhibits improved safety by providing a lock out of energy delivery at a time when anticoagulation would be indicated.

BACKGROUND OF THE INVENTION

Atrial fibrillation is probably the most common cardiac arrhythmia Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

As used herein, "atrial fibrillation" (AF) will be used to ream atrial fibrillation, flutter, or tachycardia correctable by defibrillation, low energy cardioversion, antitachycardia pacing (ATP), or drugs. "Cardioversion" will refer to any of these means.

Atral fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. However, physicians have been reluctant to implant such devices for fear that the therapy for atrial fibrillation could produce potentially lethal ventricular arrhythmias. In view of this, developers of implantable ventricular defibrillators have begun to develop dual chamber implantable defibrillators for those patients who suffer from atrial and ventricular cardiac arrhythmias.

Two proposed atrial defibrillators, although represented as being implantable, were not fully automatic, requiring human interaction for cardioverting or defibrillating the heart. Both are disclosed in U.S. Pat. No. 3,952,750 to Mirowski et al., which patent is incorporated herein by reference. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

An automatic implantable atrial defibrillator which provides a warning to the patient prior to delivery of cardioversion therapy is disclosed in U.S. Pat. No. 5,332,400 to Alferness, which patent is incorporated herein by reference.

The atrial defibrillator disclosed in Alferness includes an atrial fibrillation detector which, responsive to sensed atrial activity, determines when the atria of the heart are in need of cardioversion. When the atrial fibrillation detector determines that the atria are in fibrillation and thus in need of cardioversion, the atrial fibrillation detector causes a cardioverter stage to deliver defibrillating or cardioverting electrical energy to the atria in timed relation to a detected ventricular electrical activation (R wave) of the heart.

Unfortunately, the quantity of electrical energy which is required to cardiovert or defibrillate the atria is sufficient, in most cases, to cause a sudden pain in the patient's chest area or stun the patient. In addition, the successful cardioversion or defibrillation of the atria may also result in a rapid decrease in the patient's heart rate from a high and possibly variable heart rate. This rapid change in heart rate can, for some patients, cause discomfort or even temporary dizziness. As a result, it is highly desirable as described in the Alferness patent to provide a warning to a patient prior to the delivery of cardioverting or defibrillating electrical energy to the patient's atria. The warning is in the form of electrical energy applied to internal tissue of the patient and being of a quantity so as to be discernible by the patient without pain or other undesirable effects.

One problem with the system of Alferness is that the cardioverting energy is automatically delivered to the patient a prescribed period of time following the warning signal. Since atrial fibrillation is fairly well tolerated by most patients, it would be desirable to allow for a controllable delay in the delivery of the cardioverting energy to allow the patient to better control where he is when cardioversion occurs. Thus, while the atrial defibrillator of Alferness would warn a patient of an impending shock and allow the patient to pull over to the side of the road when driving, it would be desirable to allow patients to delay therapy for long enough for them to reach their destination and/or a safer, more comfortable location.

One problem with allowing the patient to delay delivery of therapy for atrial defibrillation is that, as mentioned above, blood clots may form in areas of stagnant blood flow as a result of prolonged atrial fibrillation. It is thus generally agreed that internal electrical cardioversion of atrial fibrillation should not be attempted without the use of anticoagulants if the patient has been in atrial fibrillation for more than 48 hours, and anticoagulation may be desirable even earlier, such as after 24 hours. It is therefore desirable to allow patient control over the timing of energy delivery for atrial defibrillation but to prevent delivery beyond a time when it is risky to deliver the therapy without the administration of anticoagulants.

SUMMARY OF THE INVENTION

The present invention provides an implantable cardiac device for providing cardioverting electrical energy to at least one atrium of a patient's heart in need of cardioversion. The device includes detecting means for detecting activity of the at least one atrium of the patient's heart, determining means responsive to the detecting means for determining when the at least one atrium of the patient's heart is in need of cardioversion, and atrial cardioverting means for applying the cardioverting electrical energy to the at least one atrium of the patient's heart when the at least one atrium is in need of cardioversion.

The device preferably includes warning means for warning the patient that at least one atrium of his heart is in need of cardioversion. This warning means may be in the form of electrical energy applied to the heart of the patient that is of insufficient quantity to intentionally cardiovert the atria but is of sufficient quantity so as to be discernible by the patient, as described in U.S. Pat. No. 5,332,400 to Alferness. The warning electrical energy is of a quantity which is less discomforting than the quantity required to cardiovert the atria. Alternatively, the warning may be in the form of an audible alarm, or of electrical energy delivered to a noncardiac region of the patient, such as muscle or nervous tissue in the region of the implanted defibrillator. A muscle stimulation electrode for such a warning system is described in U.S. Pat. No. 5,630,838 to Prutchi et al. and is incorporated herein by reference. As another alternative, warning means may be not explicitly present in the device itself, with the patient's own symptoms serving as warning means to inform him that at least one atrium of his heart is in need of cardioversion.

The invention further provides patient control means for control of the delivery of the cardioverting electrical energy to the atria of a patient's heart in need of cardioversion. The atrial cardioverting means is responsive to the determining means for determining when the at least one atrium of the patient's heart is in need of cardioversion, and to the patient control means.

The invention further provides a safety timer for measuring the time from determining when the at least one atrium is in need of cardioversion. The invention further provides deactivation means for deactivating the atrial cardioverting means at a time when anticoagulation is deemed appropriate if the atrial cardioverting means has not been activated yet. This so-called "end-of-safe time" may be up to 72 hours, and is preferably 24 to 48 hours, and most preferably 24 hours.

The present invention further provides ventricular detection means for detecting electrical activity of at least one ventricle. The ventricular detection means provides a signal for synchronizing delivery of atrial cardioversion energy, and also for determining, using ventricular determining means, whether the ventricles are themselves in need of ventricular cardioversion. The present invention further provides ventricular cardioversion means for delivering cardioverting energy to the ventricles responsive to the ventricular determining means determining that the ventricles are in need of cardioversion. The ventricular cardioverting means is not responsive to the patient control means, but is fully automatic and not deactivated following count down of the safety timer described above in conjunction with atrial cardioversion.

The present invention further provides a method of providing atrial cardioverting electrical energy to at least one atrium of a patient's heart in need of cardioversion. The method includes the steps of detecting activity of the at least one atrium of the patient's heart, determining from the detected activity when the at least one atrium of the patients heart is in need of cardioversion, providing a warning signal to the patient when the at least one atrium of the patient's heart is in need of cardioversion, providing means to the patient for controlling delivery of the atrial cardioverting electrical energy, and applying the cardioverting electrical energy to the at least one atrium of the patient's heart or deactivating the atrial cardioverting energy delivery function when a safety timer times out.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
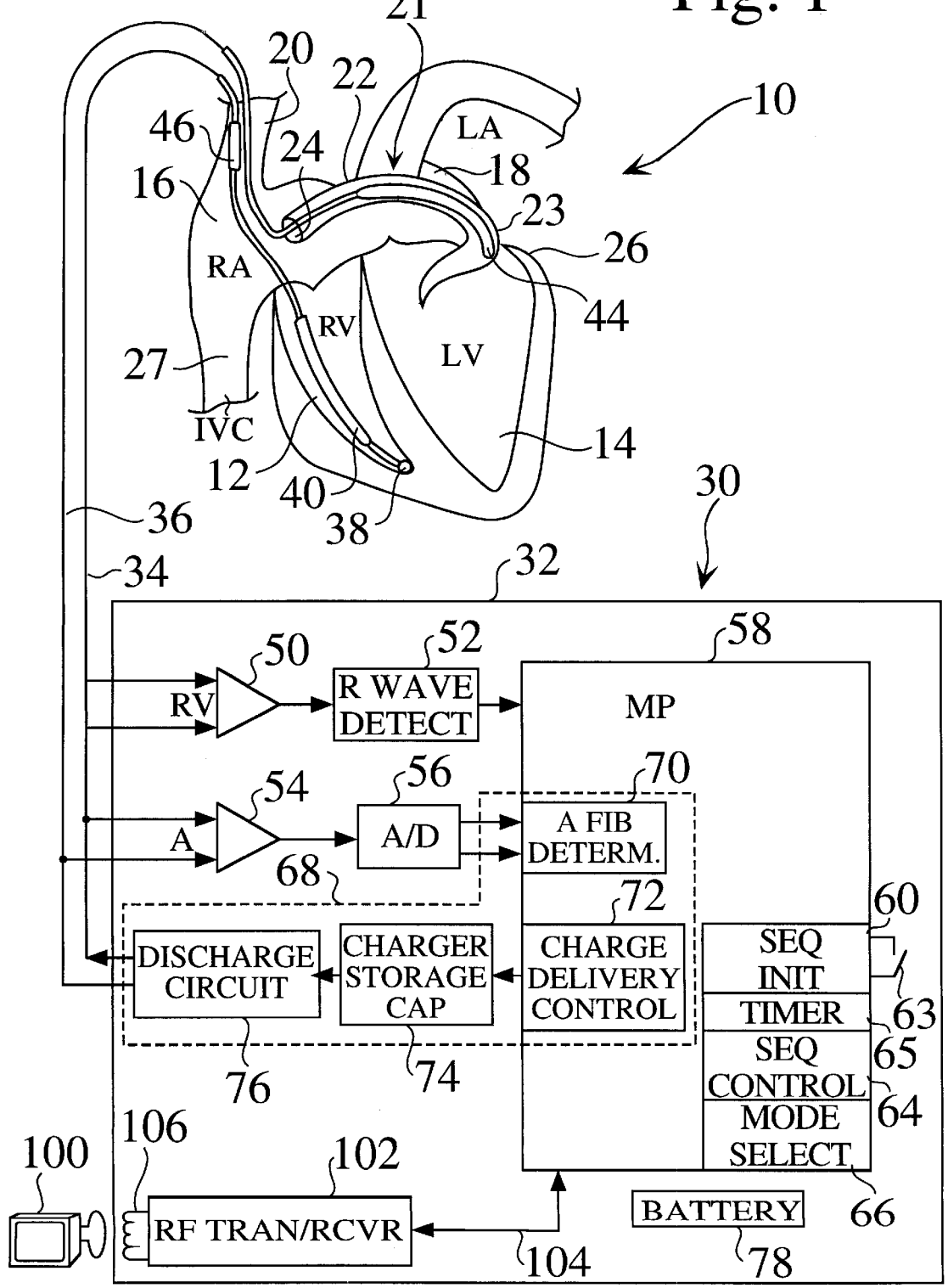
FIG. 1 s a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

FIG. 1 illustrates a fully implantable atrial defibrillator 30 embodying the present invention shown in association with a schematically illustrated human heart 10 in need of atrial fibrillation monitoring and potential cardioversion of the atria The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and a intravascular second lead 36. The enclosure 32 and first and second leads 34 and 36 are arranged to be implanted beneath the skin of a patient so as to render the atrial defibrillator 30 fully implantable. Enclosure 32 may also be electrically active to act as an electrode during atrial or ventricular defibrillation shocks, as a return electrode for pacing, or as a sensing electrode.

The endocardial first lead 34 preferably comprises an endocardial lead having electrodes 38 and 40 arranged for establishing electrical contact with the right ventricle 12 of the heart 10. The electrodes 38 and 40 permit bipolar sensing of ventricular activations in the right ventricle. Electrode 40 may also be used for ventricular defibrillation. A third electrode 46 is spaced from electrode 40 such that when electrode 38 is in contact with the right ventricle 12, electrode 46 is in the right atrium or superior vena cava. The lead 34 is preferably fed through the superior vena cava 20, into the right atrium 16 and then into the right ventricle 12, as illustrated.

The second lead 36 includes a defibrillation electrode 44. As illustrated, the second lead 36 is flexible and arranged to be passed down the superior vena cava 20, into the right atrium 16, into the coronary sinus ostium 24, and advanced into the coronary sinus channel 21 either within the coronary sinus 22 adjacent the left ventricle 14 and beneath the left atrium 18 or preferably within the great cardiac vein 23 adjacent the left ventricle 14 and beneath the left atrium 18.

Electrode 44 together with the electrode 46 provide bipolar sensing of heart activity in the atria 16 and 18. Alternatively or additionally, atrial sensing may be provided by a bipolar atrial J pacing lead (not shown) as is well known in the art Electrodes 44 and 46 further provide for the delivery of defibrillating or cardioverting electrical energy to the atria.

Within the enclosure 32, the atrial defibrillator 30 includes a first sense amplifier 50, an R wave detector 52, and a second sense amplifier 54. The first sense amplifier 50 and the R wave detector 52, together with electrodes 38 and 40 of lead 34, sense ventricular activations of the right ventricle 12. The second sense amplifier 54, together with electrodes 44 and 46, detect atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart The output of the second sense amplifier 54 is coupled to an analog-to-digital convertor 56 which converts the analog signal representative of the atrial activity of the heart being detected to digital samples for further processing.

The enclosure 32 of the atrial defibrillator 30 further includes a microprocessor 58. The microprocessor 58 may be implemented in a manner as described in U.S. Pat. No. 5,282,837, or as described in U.S. Pat. No. 5,350,404, and further as described herein after with respect to the flow diagram of FIG. 2. The implementation of the microprocessor 58 in accordance with this embodiment of the present invention results in a plurality of functional stages. The stages include a therapy sequence initiating stage 60, a safety timer 65, a therapy sequence control stage 64, a mode select stage 66, an atrial fibrillation determiner 70, and a charge and delivery control stage 72.

The microprocessor 58 is arranged to operate in conjunction with a memory (not shown) which may be coupled to the microprocessor 58 by a multiple-bit address bus (not shown) and a bidirectional multiple-bit data bus (not shown). This permits the microprocessor 58 to address desired memory locations within the memory for executing desired memory locations within the memory for executing write or read operations. During a write operation, the microprocessor stores data and operating parameters (such as a selected modality) in the memory at the addresses defined by multiple -bit addresses conveyed over the address bus and conveys the data to the memory over the multiple-bit data bus. During a read operation, the microprocessor 58 obtains data from the memory at the storage locations identified by the multiple-bit addresses provided over the address bus and receives the data from the memory over the bi-directional data bus.

For entering operating parameters into the microprocessor 58, such as mode selection, the microprocessor 58 receives programmable operating parameters, such as mode commands, from an external controller 100 which is external to the skin of the patient. The external controller 100 is arranged to communicate with a receiver/transmitter 102 which is coupled to the microprocessor 58 over a bi-directional bus 104. The receiver/transmitter 102 may be of the type well known in the art for conveying various information which it obtains from the microprocessor 58 to the external controller 100 or for receiving programming parameters, such as mode commands, from the external controller 100 which the receiver/tansmitter 102 then conveys to the microprocessor 58 for storage in the aforementioned external memory.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One such communication system is disclosed, for example, in U.S. Pat. No. 5,342,408, which is incorporated herein by reference.

The atrial defibrillator 30 further includes an intervention sequencer 68 which performs an intervention sequence, including determination that the atria are in fibrillation and cardioversion of the atria (if necessary). To that end, the intervention sequencer includes the previously mentioned atrial fibrillation determiner 70 and charge and delivery control 72, and a charger and storage capacitor circuit 74 and a discharge circuit 76. The defibrillator 30 also includes a depletable power source 78, such as a lithium battery, which provides power to the electrical components of the atrial defibrillator 30.

Each intervention sequence preferably begins with the atrial fibrillation determiner 70 determining that the atria are in need of cardioversion. This analysis is preferably performed on data obtained from sense amplifier 54 and analog-to digital convertor 56, which is prestored in the aforementioned memory (not shown) external to the microprocessor 58, but contained within the implantable enclosure 32. The atrial fibrillation determiner 70 may alternatively be of the type which performs real time analysis of the data provided by the analog-to-digital convertor 56.

If the atrial fibrillation determiner determines that the atria are in fibrillation, and in need of cardioversion, the intervention sequencer 68, under control of the sequence control stage 64, enters a therapy sequence to cardiovert the atria When the defibrillator is programmed in a patient activated mode, following the sequence initiating stage 60 initiating an intervention sequence in response to the atrial fibrillation determiner 70 determining that the atria are in need of cardioversion, a safety timer 65 is started and an alarm 67 alerts the patient. The patient may respond by generating a sequence command external to the patient, which is received by a sequence command receiver, which may be formed by a reed switch 63. The sequence command, in accordance with this embodiment, is a magnetic field generated by a magnet of the type well known in the art which is brought into close proximity with the implanted defibrillator 30. Alternatively, the sequence command may be generated by tapping on the skin overlying the defibrillator, thus creating a vibration that can be sensed by the sequence command receiver.

When the intervention sequencer 68 is not performing an intervention sequence, it is held in a deactivated or inactive state by the sequence control stage 64. When an intervention sequence is to be performed, the sequence initiating stage 60 overrides the sequence control stage 64 to cause the intervention sequencer to perform an intervention sequence.

When the defibrillator 30 is programmed in an automatic mode, the sequence initiating stage 60 initiates an intervention sequence that does not require receipt of a sequence command in order to deliver therapy.

Defibrillator 30 includes ventricular detection means 52 for detecting electrical activity of at least one ventricle, preferably using electrodes 38 and 40 on lead 34. The ventricular detection means provides a signal for synchronizing delivery of atrial cardioversion energy, and also for determining, using ventricular determining means, whether the ventricles are themselves in need of ventricular cardioversion. Defibrillator 30 also provides ventricular cardioversion means for delivering ventricular cardioverting therapy to the ventricles responsive to the ventricular determining means determining that the ventricles are in need of cardioversion. The ventricular cardioverting means may be electrical energy delivery through some combination of electrodes 40 and 46 and an electrically active enclosure 32. The ventricular cardioverting means is not responsive to the patient control means, but is fully automatic and not deactivated following count down of the safety timer described above in conjunction with atrial cardioversion.

The operation of the atrial defibrillator 30 in performing the cardioversion therapy sequence will now be described in connection with flow diagram of FIG. 2.

Figure 2:
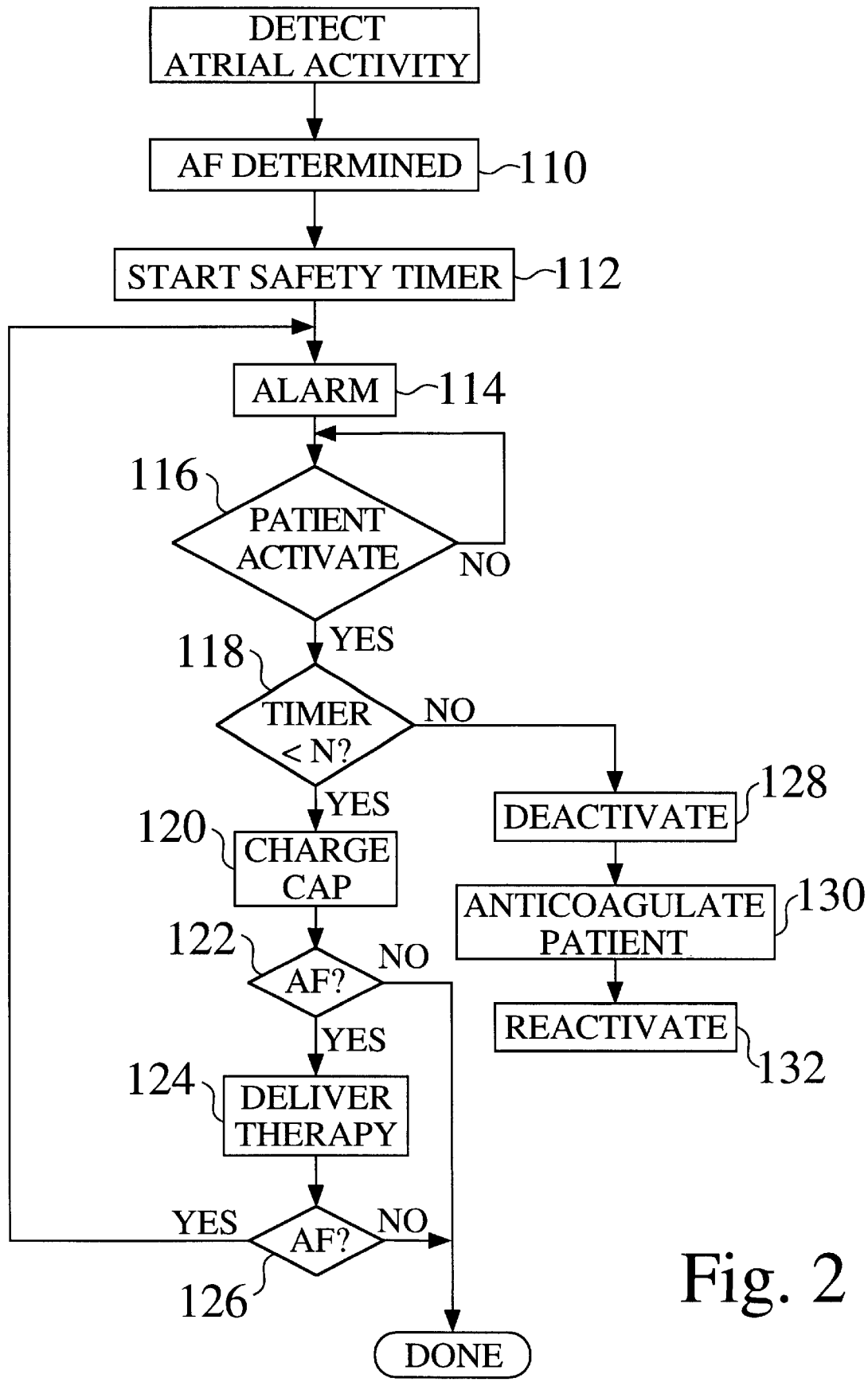
FIG. 2 is a flow diagram illustrating the manner in which the atrial defibrillator of FIG. 1 may be implemented to provide a therapy sequence which is terminated in accordance with a first embodiment of the present invention.

Referring now to FIG. 2, the atrial defibrillator 30 enters the therapy sequence upon the atrial fibrillation determiner 70 determining that the atria are in fibrillation and in need of cardioversion as denoted by step 110. In step 112, a safety timer 65 is started. In step 114, an alarm 67 alerts the patient that AF has been determined and that he must signal the atrial defibrillator 30 to employ a cardioversion shock. In step 116, the atrial defibrillator 30 monitors incoming signals to determine whether the patient has requested a shock. These signals may be magnetic and may be detected by a reed switch. When atrial defibrillator 30 determines that a shock has been requested, it also checks, in step 118, to see whether the safety timer has timed out.

If the safety timer has not timed out, in step 120, the charger and storage capacitor circuit 74 under control of the charge and delivery stage 72 charges its storage capacitor to a predetermined voltage level for cardioverting the atria of the patient' heart. When the capacitor of circuit 74 is charged, the sequence control stage 64 provides a first command to the atrial fibrillation determiner 70 to cause the atrial fibrillation detector to determine if the atria are still in need of cardioversion in step 122. If the atrial fibrillation determiner 70 determines that the atria are not in fibrillation, the sequence control stage 64 will terminate the therapy sequence. However, if it is determined in step 122 that the atria are still in need of cardioversion, the sequence control stage 64 enables the charge and delivery control stage 72 to cause the discharge circuit in step 124 to discharge the storage capacitor within circuit 74 for a predetermined time to provide a controlled discharge of cardioverting electrical energy to the atria of the heart. To that end, the discharge circuit 76 is coupled to electrode 44 and 46 for applying the cardioverting or defibrillating electrical energy to the atria, typically between 0.1 and 45 J. The discharge is preferably initiated in timed relation to an R wave detected by sense amplifier 50 and R wave detector 52. Interval timing prior to energy delivery may be performed as taught in U.S. Pat. No. 5,207,219.

As an alternative to charging the storage capacitor and delivering 0.1 to 45 J electrical energy to the atria, cardioversion therapy may be in the form of antiarrhythmic drug delivery, as described in U.S. Pat. No. 5,527,344 to Arzbaecher et al., entitled "Pharmacologic Atrial Defibrillator and Method,", which is incorporated herein by reference. As a further alternative, cardioversion therapy may be in the form of atrial antitachycardia pacing (ATP), as is well known in the art While some publications in the literature have noted thromboembolism occurring with electrical cardioversion but not chemical or spontaneous, others have observed thromboembolism resulting from return to normal sinus rhythm following electrical, chemical, and spontaneous conversion of AF. Therefore, a safety timer and cardioversion deactivating means is likely to be important for all types of cardioversion, including high energy electrical, chemical, and ATP.

Following therapy delivery, the atrial fibrillation determiner 70 once again, under command from the sequence control stage 64, determines if the atria are in fibrillation in accordance with step 126. If the atria are still in fibrillation, the sequence control stage returns to step 114 to once again alert the patient that he must request a shock from the atrial defibrillator 30. In step 120, the storage capacitor may be charged to an incrementally increased voltage level in anticipation of again applying cardioverting electrical energy to the atria of the heart. However, if in step 126 the atrial fibrillation determiner 70 does not determine that the atria are in fibrillation, the atrial fibrillation episode will be considered to have been terminated by the last cardioversion.

In step 118, if it were determined that the safety timer had reached its programmed "end-of-safe time", typically 24 hours, the atrial defibrillator would be deactivated in step 128, and atrial shock therapy would not be delivered by the device until it is reactivated in step 132. Reactivation in step 132 is accomplished by a physician using external controller 100, and only after determining it is safe to do so, such as by administering anticoagulation in step 130, or determining thromboembolic risk is low using transesophageal echocardiography or other means.

Hence, as can be seen from the foregoing, once atrial fibrillation is first detected in step 110, while in manual mode, the sequence control allows application of cardioverting therapy until either the heart is successfully cardioverted or until the safety timer reaches a preselected time such as 24 hours to allow for anticoagulation.

Following administering anticoagulation in step 130 or determining low risk of thromboembolism, if the patient is still in AF, the device may be reactivated in step 132, then allowed to determined that the patient is still in AF in step 110. The device 30 would then continue the intervention sequence to deliver cardioversion therapy. As an alternative to allowing device 30 to redetect and automatically terminate the AF episode, other means may be employed to terminate it. For example, chemical cardioversion or externally applied electrical cardioversion may be used. As another alternative, device 30 may be capable of delivering a programmed command (PC) shock, initiated by commands provided to the external controller 100. In that case, the physician would enter a command to the external controller 100 to trigger a shock delivered by device 30, without requiring AF detection, safety timer, alarm, or patient activation.

Another feature of the present invention is that following reactivation in step 132, the safety timer 65 may be inhibited for a programmable period of time, such as 3 to 4 weeks, during which time the patient will be assumed to be anticoagulated. During this time, the patient would be allowed to activate therapy delivery following determination that he is in AF, even if the determination were made greater than 24 hours prior to patient activation.

Figure 3:
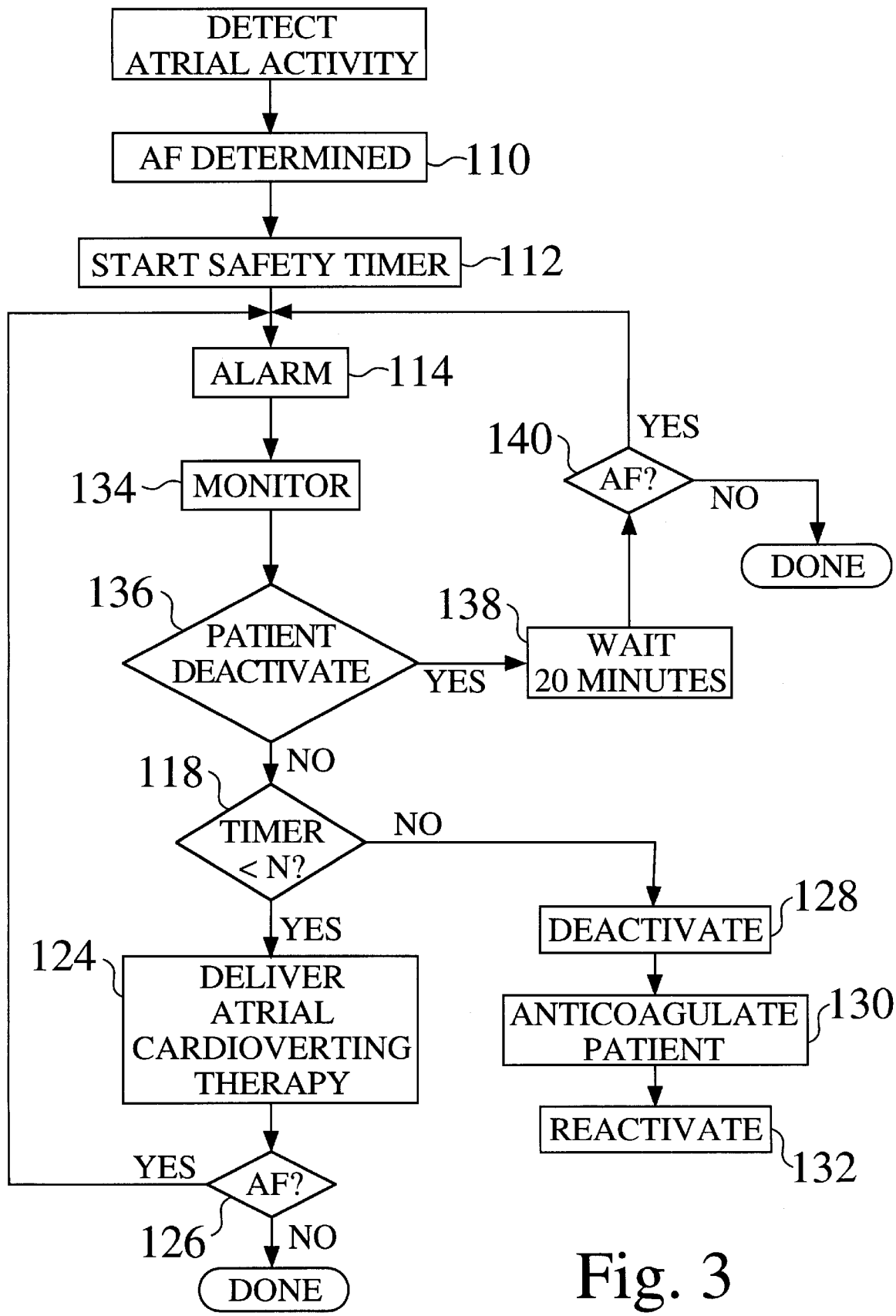
FIG. 3 is a flow diagram illustrating of the manner in which the atrial defibrillator of FIG. 1 may be implemented to provide a therapy sequence which is terminated in accordance a second embodiment of the present invention.

FIG. 3 is a flow diagram illustrating another mode of operation of the atrial defibrillator 30 in performing the cardioversion therapy sequence. The major difference between the operation mode shown in FIG. 3 as compared with FIG. 2 is that the patient control means is means to inactivate cardioversion therapy instead of to activate it. As in FIG. 2, the atrial defibrillator 30 enters the therapy sequence upon the atrial fibrillation determiner 70 determining that the atria are in fibrillation and in need of cardioversion as denoted by step 110. In step 112, a safety timer 65 is started. In step 114, an alarm 67 alerts the patient that AF has been determined, and that the defibrillator 30 will be delivering therapy shortly unless he signals the atrial defibrillator 30 to delay it. In step 134, defibrillator 30 monitors incoming signals during a preprogrammed monitoring period, say 30 seconds, to determine whether the patient has requested delay of therapy. Again, these signals may be magnetic and may be detected by a reed switch, or may be vibrations produced by tapping on the skin overlying the defibrillator. When atrial defibrillator 30 determines that a shock has been delayed, it waits a preprogrammed delay period, say 20 minutes. At the end of 20 minutes, it rechecks for AF at step 140. If the patient is still in AF, an alarm again alerts the patient to delay therapy or to allow the device to deliver therapy.

If, following the monitoring period, no signal has been given by the patient to delay therapy, defibrillator 30 checks, in step 118, to see whether the safety timer has timed out. If the safety timer has not timed out, atrial cardioversion therapy is delivered in step 124. As described above, the therapy may be in the form of electrical shocks, antiarrhytmic drug delivery, or ATP. The intervention sequence continues as in FIG. 2.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable cardiac device for providing cardioverting therapy to a patient when at least one atrium of the patient's heart is in need of cardioversion, said device comprising:

atrial detecting means for detecting activity of the at least one atrium;

atrial arrhythmia determining means responsive to said atrial detecting means for determining a time when the at least one atrium is in need of cardioversion;

patient control means for allowing patient controlled delivery of the cardioverting therapy;

atrial cardioverting means responsive to said atrial arrhythmia determining means and to said patient control means for applying the cardioverting therapy when the at least one atrium is in need of cardioversion;

a safety timer for measuring time from the determining of said time when the at least one atrium is in need of cardioversion to an "end-of-safe time"; and deactivation means for deactivating said cardioverting means from delivering the cardioverting therapy when said safety timer reaches said "end-of-safe time".

2. The device of claim 1 and further including warning means for alerting the patient that the at least one atrium is in need of cardioversion.

3. The device of claim 1 wherein said "end-of-safe time" is 24 hours.

4. The device of claim 1 wherein said "end-of-safe time" is programmable between 24 hours and 72 hours.

5. The device of claim 1 wherein said patient control means for allowing patient controlled delivery of the cardioverting therapy comprises means for triggering the delivery of the cardioverting therapy.

6. The device of claim 1 wherein said patient control means for allowing patient controlled delivery of the cardioverting therapy comprises means for delaying the delivery of the cardioverting therapy.

7. The device of claim 1 and further comprising:

ventricular detecting means for detecting electrical activity of at least one ventricle;

ventricular arrhythmia determining means responsive to said ventricular detecting means for determining a time when the at least one ventricle is in need of cardioversion;

ventricular cardioverting means responsive to said ventricular arrhythmia determining means for applying the ventricular cardioverting therapy to the at least one ventricle when the at least one ventricle is in need of cardioversion.

8. The device of claim 1 wherein said atrial cardioverting means comprises delivery of electrical energy of between 0.1 and 45 J to the atria.

9. The device of claim 1 wherein said atrial cardioverting means comprises delivery of antitachycardia pacing pulses to the atria.

10. The device of claim 1 wherein said atrial cardioverting means comprises delivery of at least one antiarrhythmic drug.

11. A method for providing cardioverting therapy to the atria of a heart comprising the steps of:

(a) detecting activity of the atria with an atrial defibrillator having atrial cardioverting means for delivering atrial cardioverting therapy;

(b) determining a time when the atria are in need of cardioversion;

(c) measuring time from the determining of the time when the atria are in need of cardioversion to an "end-of-safe time";

(d) alerting the patient that the atria are in need of cardioversion; and (e) deactivating atrial cardioverting means for delivering atrial cardioverting therapy when said safety timer reaches said "end-of-safe time".

12. The method of claim 11 and further comprising after said step (d):

(f) providing a signal to an implantable cardioverter to deliver atrial cardioverting therapy; and (g) delivering atrial cardioverting therapy in response to the signal provided in step (f).

13. The method of claim 11 wherein said "end-of-safe time" is 24 hours from said determining step (b).

14. The method of claim 11 wherein said "end-of-safe time" is programmed between 24 and 72 hours.

15. The method of claim 11 wherein said step (f) of providing a signal to an implantable cardioverter further comprises the patient tapping skin overlying the implantable cardioverter.

16. The method of claim 11 wherein said step (f) of providing a signal to an implantable cardioverter further comprises applying a magnet adjacent to skin overlying the implantable cardioverter.

17. The method of claim 11 and further comprising after deactivating step (e), the step of:

(h) administering anticoagulants to the patient.

18. The method of claim 17 and further comprising after anticoagulant step (h), the step of:

(i) applying cardioversion therapy chosen from the group consisting of chemical cardioversion, externally applied cardioversion, and programmed shock cardioversion.

19. The method of claim 17 and further comprising after anticoagulant step (h), the step of:

(j) reactivating said cardioverting means for delivering the cardioverting therapy;

(k) repeating steps (a) through (d).

* * * * *